(12) United States Patent
Nakamura et al.

(10) Patent No.: US 8,159,232 B2
(45) Date of Patent: Apr. 17, 2012

(54) FUEL PROPERTY SENSOR

(75) Inventors: Hiroshi Nakamura, Kariya (JP);
Akikazu Uchida, Obu (JP); Daisuke Shikanai, Tokai (JP)

(73) Assignee: Denso Corporation, Kariya (JP)

( * ) Notice: Subject to any disclaimer, the term of this patent is extended or adjusted under 35 U.S.C. 154(b) by 267 days.

(21) Appl. No.: 12/730,436

(22) Filed: Mar. 24, 2010

(65) Prior Publication Data

US 2010/0244857 A1    Sep. 30, 2010

(30) Foreign Application Priority Data

Mar. 24, 2009    (JP) .................................... 2009-72608

(51) Int. Cl.
*G01R 27/26* (2006.01)
*G01N 33/26* (2006.01)

(52) U.S. Cl. ........ 324/663; 324/685; 324/690; 73/53.05

(58) Field of Classification Search ................ 324/663, 324/684–686, 690, 698; 73/53.01, 53.05
See application file for complete search history.

(56) References Cited

U.S. PATENT DOCUMENTS

| | | | | |
|---|---|---|---|---|
| 4,058,787 | A | * | 11/1977 | Ichikawa et al. ............ 338/22 R |
| 5,182,523 | A | * | 1/1993 | Ertel et al. .................... 324/663 |
| 5,929,754 | A | * | 7/1999 | Park et al. .................... 324/663 |
| 6,553,812 | B2 | * | 4/2003 | Park et al. .................... 324/663 |
| 7,030,629 | B1 | | 4/2006 | Stahlmann et al. | |
| 2010/0014557 | A1 | | 1/2010 | Tomioka et al. | |

FOREIGN PATENT DOCUMENTS

| | | |
|---|---|---|
| JP | 29-10499 | 8/1954 |
| JP | 1-163862 | 11/1989 |
| JP | 3-118432 | 5/1991 |
| JP | 6-249816 | 9/1994 |
| JP | 11-295258 | 10/1999 |
| JP | 3110103 | 4/2005 |
| JP | 2007-120963 | 5/2007 |

OTHER PUBLICATIONS

Japanese Office Action dated Dec. 16, 2010, issued in corresponding Japanese Application No. 2009-072608, with English Translation.

* cited by examiner

*Primary Examiner* — Timothy J Dole
(74) *Attorney, Agent, or Firm* — Nixon & Vanderhye PC

(57) ABSTRACT

In a fuel property sensor, a pair of first and second electrodes is arranged in a fuel chamber to measure an electric capacitance, thereby detecting a mixing ratio of alcohol to gasoline in a fuel of the fuel chamber. An outer wall surface of the first electrode is exposed in the fuel, and a sensing portion contacts an inner wall surface of the first electrode to detect a temperature of the fluid via the first electrode. One end portion of a lead is connected to the sensing portion and the other end portion thereof is connected to a plate portion attached to a housing. Furthermore, an elastic deformation portion is provided as a part of the lead to be elastically deformed, and to cause the sensing portion to be biased in a direction on which the sensing portion contacts the inner wall surface of the first electrode.

8 Claims, 4 Drawing Sheets

FUEL PROPERTY SENSOR

CROSS REFERENCE TO RELATED APPLICATION

The present application is based on Japanese Patent Application No, 2009-72608 filed on Mar. 24, 2009, the disclosure of which is incorporated herein by reference in its entirety.

FIELD OF THE INVENTION

The present invention relates to a fuel property sensor which detects a fuel property of a vehicle, for example.

BACKGROUND OF THE INVENTION

Recently, alcohol-blended gasoline is used as fuel of vehicles in order to protect the environment. In this case, it is necessary to set an appropriate fuel injection amount and an ignition time based on a mixed ratio of the alcohol in the gasoline. Thus, in the vehicles, a sensor is generally provided so as to detect the mixed ratio of the alcohol to the gasoline. For example, in U.S. Pat. No. 7,030,629, an electrical characteristic of a fluid is measured so as to detect a fluid property, and the detected value is corrected based on a fluid temperature, thereby improving the detecting accuracy.

In the sensor described in U.S. Pat. No. 7,030,629, the electrical characteristic of the fluid to be detected is detected by using an electrode portion exposed to the fluid, and then the fluid property is determined based on the detected value and a fluid temperature measured by a temperature sensor via the electrode portion. The electrode portion and the temperature sensor are held inside of a housing exposed to the atmosphere. Therefore, heat is transmitted from the atmosphere via the housing, and thereby it is difficult to accurately measure the fuel temperature. When the fluid temperature cannot be accurately measured, the fluid property cannot be accurately detected.

In a fuel property sensor described in JP 1-163862U, an electrode portion is configured to have a hollow structure, and a temperature sensor is accommodated in the electrode portion. Thus, the temperature sensor can detect the temperature of the fuel without receiving heat from the atmosphere.

In the fuel property sensor described in JP 1-163862U, a sensing portion at a tip end of the temperature sensor is made to contact an inner wall of the electrode portion. Thus, if a dimension difference is caused in the electrode portion or the temperature sensor, it may difficult for the sensing portion to accurately contact the inner wall of the electrode portion, and thereby it may difficult to accurately measure the fuel temperature by using the temperature sensor. Furthermore, because the coefficient of linear expansion is generally different between the electrode portion and the temperature sensor, a stress may be applied to a conductive wire of the temperature sensor fixed to a substrate, and thereby the conductive wire of the temperature sensor may be damaged.

SUMMARY OF THE INVENTION

In view of the above points, it is an object of the present invention to provide a fuel property sensor, which can improve detection accuracy of a fuel temperature, thereby improving detection accuracy of a fuel property.

According to an aspect of the present invention, a fuel property sensor includes a housing defining a fuel chamber in which a fuel passes, a pair of first and second electrodes arranged in the fuel chamber to measure an electric capacitance therebetween so as to detect a mixing ratio of alcohol to gasoline in the fuel, a sensing portion contacting an inner wall surface of the first electrode, to detect a temperature of the liquid fluid via the first electrode, and a lead configured to support the sensing portion. In the fuel property sensor, the lead has one end portion connected to the sensing portion and the other end portion connected to a plate portion attached to the housing, and the first electrode is located such that an outer wall surface of the first electrode is exposed to the fuel. Furthermore, an elastic deformation portion is provided as a part of the lead, and is configured to be elastically deformed and to cause the sensing portion to be biased in a direction on which the sensing portion contacts the inner wall surface of the first electrode.

Thus, the sensing portion is pressed to the inner wall surface of the first electrode portion by using the elastic force (biasing force) of the elastic deformation portion, and thereby a contact state of the sensing portion to the inner wall surface of the first electrode can be accurately maintained. As a result, detection accuracy of the sensing portion for detecting the fluid temperature can be improved, thereby improving detection accuracy of a fuel property.

Furthermore, because the elastic deformation portion is provided as a part of the lead, it can prevent a breaking of the lead, even when a stress is applied to the lead due to a difference of the coefficient of liner expansion between the first electrode and the lead.

For example, a part of the lead may be bent to have a bent portion, and the elastic deformation portion may be configured by the bent portion. Furthermore/Alternatively, a holder fixed to the plate member may be disposed to be engaged with the inner wall surface of the first electrode. In this case, the holder has a receiving portion in which the elastic deformation portion is held to be electrically insulated from the first electrode. Furthermore, the holder may have therein a communication passage communicating with the receiving portion. In this case, the lead penetrates through the communication passage.

Furthermore/Alternatively, the first electrode may be provided with an approximately cylindrical wall portion with a bottom, to define therein an inner space partitioned from the fuel in the fuel chamber. In this case, the sensing portion is disposed in the inner space of the cylindrical wall portion of the first electrode to contact an inner surface of the cylindrical wall portion of the first electrode. In addition, the sensing portion may be disposed to contact the inner surface of the bottom of the cylindrical wall portion of the first electrode, and the lead may extend in the cylindrical wall portion of the first electrode from the sensing portion in an axial direction.

Furthermore/Alternatively, the second electrode may be located to opposite to the first electrode. For example, the second electrode may have an approximately cylindrical shape, and the first electrode may be disposed inside of the second electrode.

In the fuel property sensor, a circuit element portion may be configured to correct the measured electric capacitance based on the temperature detected by the sensing portion, so as to determine the mixing ratio of the alcohol to the gasoline.

BRIEF DESCRIPTION OF THE DRAWING

The above and other objects, features and advantages of the present invention will become more apparent from the following detailed description made with reference to the accompanying drawing. In the drawing.

DETAILED DESCRIPTION OF THE PREFERRED EMBODIMENTS (Embodiment)

Hereinafter, an embodiment of the present invention will be described with reference to the drawings.

In the present embodiment, the present invention is typically applied to a fuel property sensor which uses a fuel as a detection subject, in which an alcohol is mixed in gasoline. The fuel property sensor measures an electric capacitance in accordance a relative permittivity of the fuel as an electrical characteristic, and detects a mixing ratio of the alcohol to the gasoline as a fuel property.

First, a basic structure of a fuel property sensor 1 of the embodiment will be described with reference to FIGS. 1-4.

Figure 1:
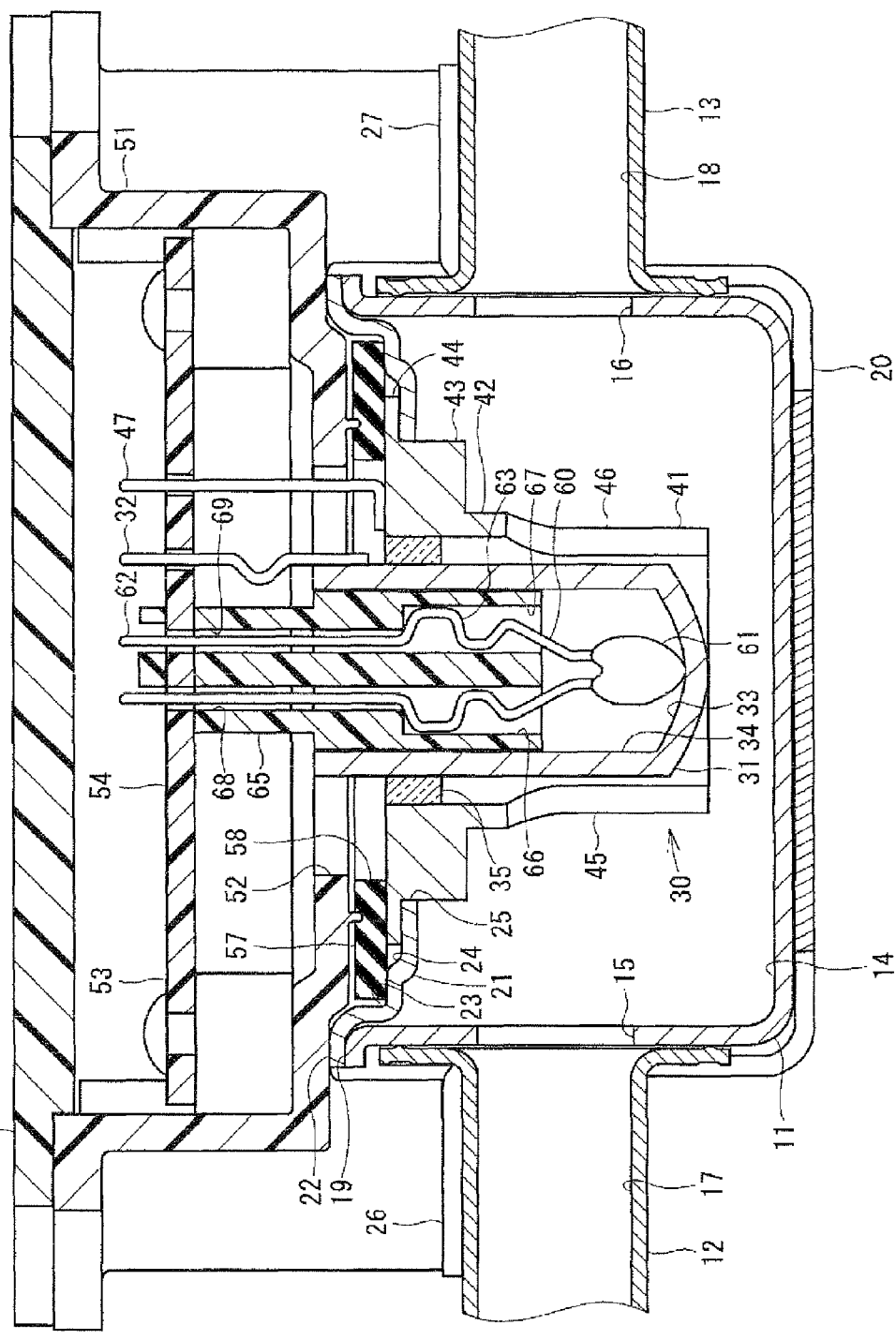
FIG. 1 is a schematic cross-sectional view showing a fuel property sensor according to an embodiment of the present invention.
Figure 2:
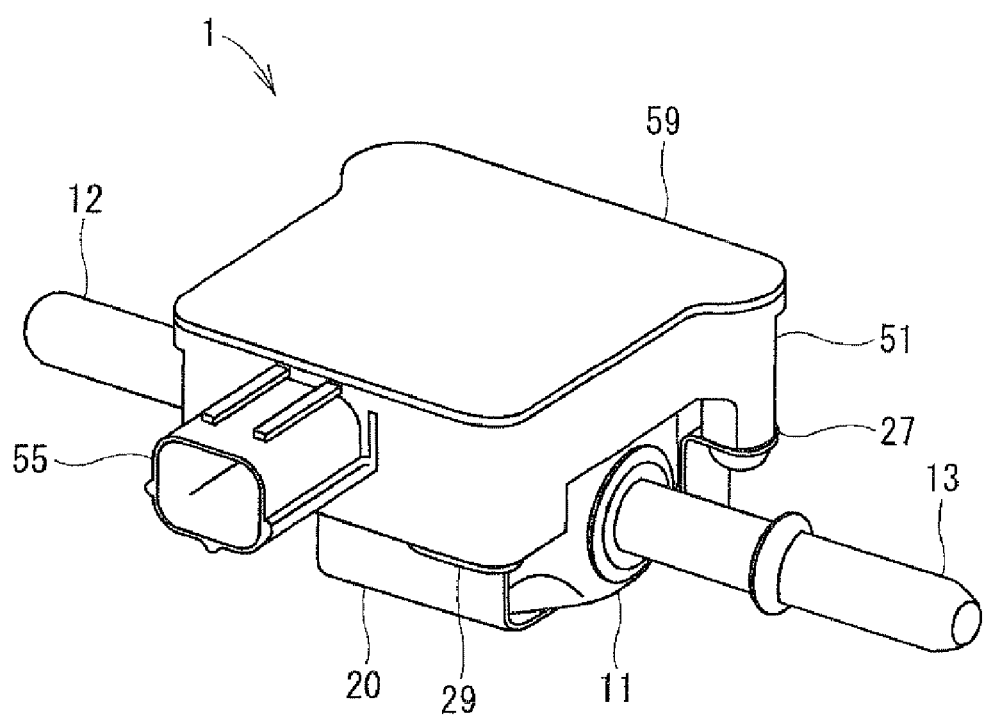
FIG. 2 is a perspective view showing the fuel property sensor according to the embodiment of the present invention.

As shown in FIG. 1, the fuel property sensor 1 includes a first housing 11, an electrode portion 30, a second housing 51 and the like.

The first housing 11 is made of a metal such as stainless or a resin or the like, and is formed approximately into a one-side open cylindrical shape having a bottom. The first housing 11 is provided with a fuel chamber 14 therein, and fuel pipes 12, 13 are bonded and fixed to side walls of the first housing 11, respectively. A fuel passage 17 is provided in an inner portion of the fuel pipe 12 to communicate with a fuel opening 15 opened at one side wall of the first housing 11, and a fuel passage 18 is provided in an inner portion of the fuel pipe 13 to communicate with a fuel opening 16 opened at another side wall of the first housing 11.

The fuel pipes 12, 13 are connected respectively to fuel pipes coupled to a fuel tank (not shown) or coupled to an injector (not shown). Thus, the fuel flowing in the fuel pipes 12, 13 can flow into the fuel chamber 14.

Figure 3:
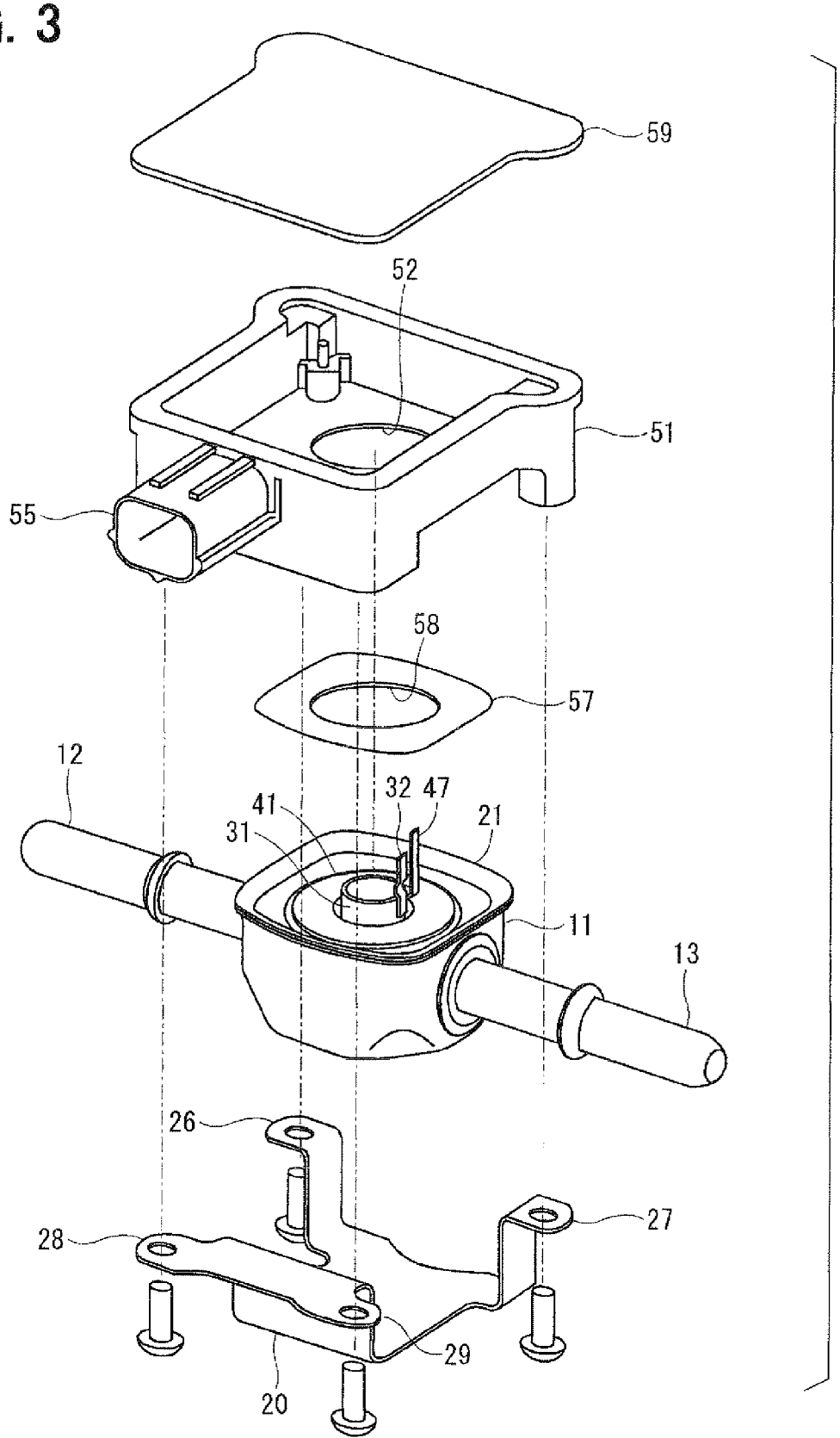
FIG. 3 is a disassembled perspective view showing the fuel property sensor according to the embodiment of the present invention.

A bracket 20 is located to cover the bottom portion of the first housing 11, as shown in FIGS. 1 and 3. The bracket 20 is provided with a plurality of flanges 26, 27, 28, 29, and holes are provided in the flanges 26, 27, 28, 29, respectively. The bracket 20 is screwed to a second housing 51 at the flanges 26, 27, 28, 29, so that the first housing 11 is assembled to the second housing 51 via the flanges 26, 27, 28, 29 of the bracket 20.

A cover member 21 is formed into an approximate circular shape by using a metal such as stainless. The cover member 21 is provided with a flange portion 22, a first step portion 23 having a radial dimension of an open area smaller than that of the flange portion 22, and a second step portion 24 having a radial dimension of an open area smaller than that of the first step portion 23. An approximately circular receiving hole 25 is provided in the second step portion 24. The cover member 21 is melted and fixed to a flange portion 19 provided at an open side of the first housing 11.

The electrode portion 30 includes a pair of a first electrode 31 and a second electrode 41. The first electrode 31 is made of a metal such as a stainless, for example, and is formed into an approximately cylindrical shape having a closed bottom. A thermistor 60 is accommodated in a cylindrical space of the first electrode 31.

Figure 4:
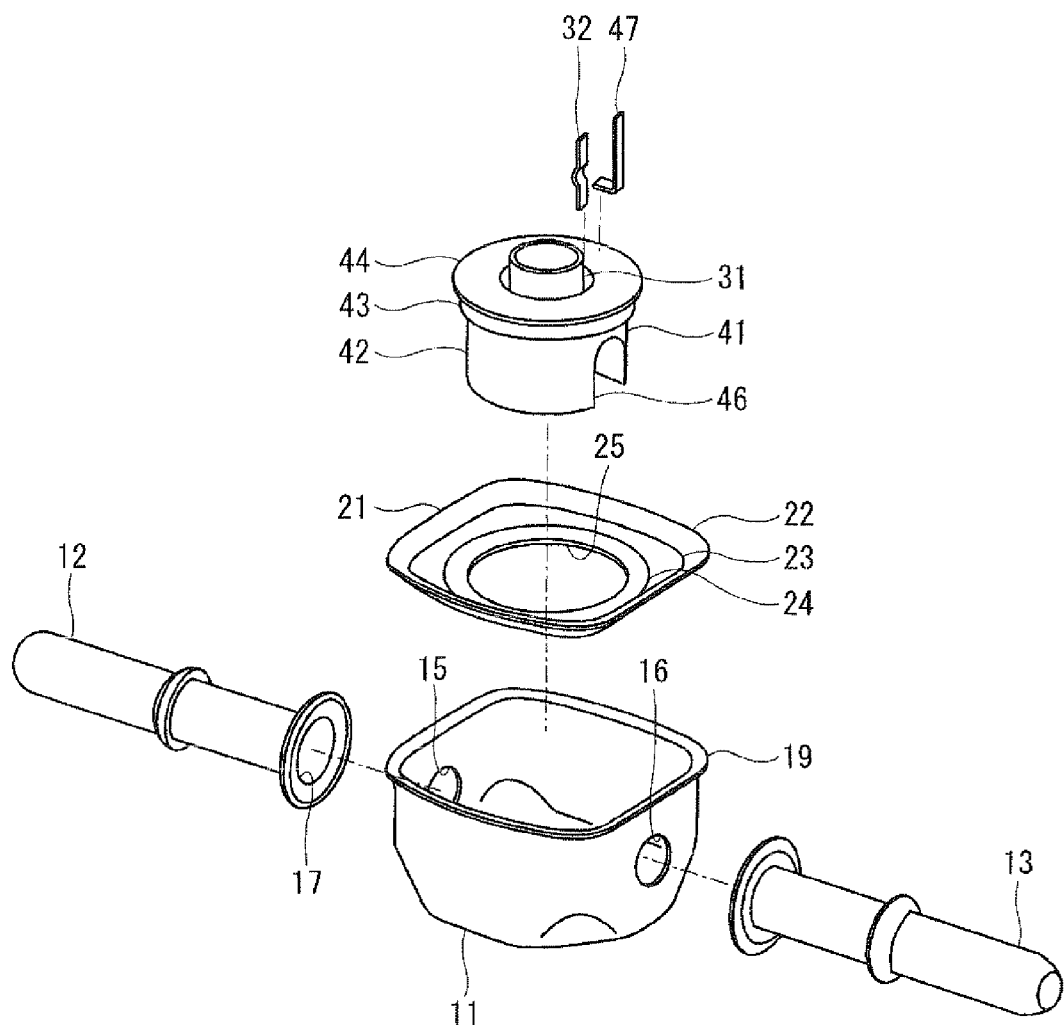
FIG. 4 is a disassembled perspective view showing a first housing and an electrode portion in the fuel property sensor according to the embodiment of the present invention.

The second electrode 41 is made of a metal such as a stainless, and is formed into an approximately cylindrical shape having an open bottom. The second electrode 41 is located outside of the first electrode 31. The second electrode 41 includes a small-diameter portion 42, a middle-diameter portion 43 having a diameter larger than the small-diameter portion 42, and a large-diameter portion 44 having a diameter larger than that of the middle-diameter portion 43. A side wall of the small-diameter portion 42 is provided with cut portions 45, 46 at two positions, each of which is formed into approximately a U-shape, as shown in FIG. 4. A clearance between the first electrode 31 and the large-diameter portion 44 of the second electrode 41 is air-tightly sealed by a glass member 35.

The electrode portion 30 including the pair of the first and second electrodes 31, 41 is located in the receiving hole 25 of the cover member 21 inside of the housing 11, to be engaged with the receiving hole 25 of the cover member 21. More specifically, the middle-diameter portion 43 and the small-diameter portion 42 of the second electrode 41 are arranged inside of the receiving hole 25, and an outer step portion between the middle-diameter portion 43 and the larger-diameter portion 44 is engaged with the cover member 21 at a side of the receiving hole 25. Thus, an opening portion of the first housing 11 is liquid-tightly sealed by the cover member 21 and the electrode portion 30. The first electrode 31, and the small-diameter portion 42 and the middle-diameter portion of the second electrode 41 are exposed in the fuel within the fuel chamber 14, and are adapted to measure the electrical characteristics of the fuel.

The second housing 51 is arranged adjacent to the cover member 21 of the first housing 11, as shown in FIG. 1. As shown in FIG. 3, the second housing 51 is formed approximately into a one-side opened cylindrical shape having a bottom. The second housing 51 is made of a resin or the like, and is formed into approximately a one-side opened cylindrical shape. A substrate 53 is located in the second housing 51, as shown in FIG. 1. The substrate 53 is provided with a circuit element portion 54 in which a conversion circuit for converting between the electric capacitance (C) and the voltage (V), or a sampling circuit, or the like is provided.

The thermistor 60 is electrically connected to the substrate 53, as a part of the circuit element portion 54. A first conductive wire 32 electrically connected to the first electrode 31, and a second conductive wire 47 electrically connected to the second electrode 41 are electrically connected to the substrate 53, respectively, as a part of the circuit element portion 54. The substrate 53 is electrically connected to a terminal (not shown) of a connector 55 located at a side surface of the second housing 51, and the connector 55 is connected to an ECU by using a wire (not shown).

An approximately circular receiving hole 52 is provided in a bottom portion of the second housing 51. An elastic member 57 has therein an approximately circular hole 58 that has a radial dimension approximately equal to the radial dimension of the receiving hole 52. The elastic member 57 is attached to a bottom surface of the second housing 51, and is inserted between the cover member 21 and the bottom surface of the second housing 51 to contact the bottom surface of the second housing 51 and the first step portion 23 of the cover member 21. The elastic member 57 is made of an insulation material such as an elastomer, for example, and is formed into approximately a circular shape. The elastic member 57 is located to prevent a heat transmission from the substrate 53 toward the inside of the first housing 11. An opening of the second housing 51 is tightly covered by a cover 59.

The thermistor 60 is located inside of the first electrode 31. The thermistor 60 includes a sensing portion 61 and a lead 62. The thermistor 60 is adapted as a part of the circuit element portion 54, and the lead 62 is electrically connected to the substrate 53 by soldering, for example, at a side opposite to the sensing portion 61. Therefore, the lead 62 can support the sensing portion 61. The sensing portion 61 is arranged to contact an inner bottom surface 33 of the cylindrical first electrode 31. Thus, a fuel temperature in the fuel chamber 14 is transmitted to the sensing portion 61 via the first electrode 31, so that the fuel temperature in the fuel chamber 14 can be measured by the sensing portion 61.

When a voltage is applied between the first electrode 31 and the second electrode 41, the first electrode 31 and the second electrode 41 are adapted as electrodes of a condenser using the fuel in the fuel chamber 14 as a dielectric material.

A relative permittivity of the fuel in the fuel chamber 14 is changed based on a mixing ratio of ethanol to gasoline. For example, in a case where the relative permittivity of the gasoline is about 2 and the relative permittivity of ethanol is about 25, the relative permittivity of the ethanol blended fuel is changed approximately in a range between 2 to 25, in accordance with the mixing ratio of the ethanol to the gasoline. The electric capacitance is a value corresponding to the relative permittivity. Thus, by measuring the electric capacitance between the first electrode 31 and the second electrode 41, the mixing ratio of the ethanol to the gasoline can be determined.

The electric capacitance is changed based on the fuel temperature at the measuring time. In the present embodiment, a measured value of the electric capacitance between the first electrode 31 and the second electrode 41 is corrected in the circuit element portion 54 based on the fuel temperature detected by the thermistor 60, and then the mixing ratio of the ethanol to the gasoline is determined based on the corrected electric capacitance in the circuit element portion 54. Thereafter, the determined result is transmitted to the ECU.

Because the detected value of the mixing ratio of the ethanol to the gasoline is corrected based on the fuel temperature, the ECU can accurately set an appropriate fuel injection amount and an ignition timing based on the determined value.

Next, the structure of the fuel property sensor 1 of the present embodiment will be described in detail. As shown in FIG. 1, an elastic deformation portion 63 is provided as a part of the lead 62 of the thermistor 60, in the fuel property sensor 1. In the example of FIG. 1, a part of the lead 62 is bent to have a bent portion so as to configure the elastic deformation portion 63. The elastic deformation portion 63 is provided in the lead 62 to cause the sensing portion 61 to be biased in a direction so that the sensing portion 61 tightly contacts the bottom inner surface 33 of the cylindrical first electrode 31 by using the biasing force of the elastic deformation portion 63. The lead 62 is assembled and connected to the substrate 53 in a constriction state of the elastic deformation portion 63.

A holder 65 is provided to hold the thermistor 60. One end of the holder 65 is fixed to the substrate 53, and the thermistor 60 is held by the holder 65 to be engaged with the holder 65. The holder 65 is made of a resin, and two parts of the elastic deformation portion 63 are accommodated in two receiving portions 66, 67 of the holder 65, respectively. Therefore, the elastic deformation portion 63 of the lead 62 can be electrically insulated by the holder 65, so as to prevent the elastic deformation portion 63 from directly contacting the inner wall surface 34 of the first electrode 31.

The holder 65 is provided with two communication passages 68, 69 communicating with the two receiving portions 66, 67, respectively. Thus, two wire parts of the lead 62 including the elastic deformation portion 63 are electrically insulated by the holder 65, respectively. The communication passages 68, 69 are provided in the holder 65 such that a diameter of each communication passage 68, 69 is slightly larger than a wire diameter of the two part of the lead 62. Thus, the position of the lead 62 is set when the lead 62 passes through the communication passages 68, 69, and thereby the lead 53 can be accurately assembled to the substrate 53 at a predetermined position.

Thus, by the biasing force (elastic force) of the elastic deformation portion 63, the sensing portion 61 is pressed to the bottom inner surface 33 of the cylindrical first electrode 31, thereby keeping a contact state at which the sensing portion 61 tightly contacts the bottom inner surface 33 of the cylindrical first electrode 31. Therefore, it can prevent the sensing portion 61 from being separated from the bottom inner surface 33 of the cylindrical first electrode 31, thereby improving a detection accuracy of the fuel temperature in the sensing portion 61. As a result, a detection accuracy in the fuel property of the fuel property sensor can be improved.

In the fuel property sensor 1 of the present embodiment, even when the coefficient of liner expansion is different between the first electrode 31 and the lead 62 so as to apply a stress to the lead 62, it can prevent breaking of the lead 62.

Furthermore, because a part of the lead 62 is bent to configure the elastic deformation portion 63 by using the bent portion, the elastic deformation portion 63 can be easily formed as compared with a case where the elastic deformation portion 63 is a member formed separated from the lead 62.

In the fuel property sensor 1 of the present embodiment, because the two parts of the elastic deformation portion 63 are received respectively in the receiving portions 66, 67 of the holder 65 to be elastically insulated from the first electrode 31, it can prevent the elastic deformation portion 63 from contacting the first electrode 31.

Because the position of the lead 62 can be determined while the wires of the lead 62 pass through the communication passage 68, 69 of the holder 65, the assembling performance of the thermistor 60 to the substrate 53 can be improved.

In the fuel property sensor 1 of the present embodiment, the first electrode 31 has approximately a cylindrical shape having a bottom, the sensing portion 61 is arranged to contact the bottom inner surface 33, and the fuel temperature flowing in the fuel chamber 14 is detected via the first electrode 31. Because the first electrode 31 can be immersed in the liquid fuel, the fuel temperature can be accurately detected via the first electrode 31. Thus, even when the size of the first electrode 31 is made small, an exposed area of the first electrode 31 in the liquid fuel can be secured, thereby reducing the size of the electrode portion 30.

In the fuel property sensor 1 of the present embodiment, the second electrode 41 is formed into approximately a cylindrical shape, and the first electrode 31 having the bottom is located inside of the second electrode 41 to be exposed to the liquid fuel from a bottom side of the second electrode 41.

The present invention is not limited to the above embodiment.

For example, according to an aspect of the present embodiment, a fuel property sensor (1) includes a housing defining a fuel chamber (14) in which a liquid fuel passes, a pair of first and second electrodes (31, 41) arranged in the fuel chamber (14) to measure an electric capacitance therebetween so as to detect a mixing ratio of alcohol to gasoline in the liquid fuel, a sensing portion (61) contacting an inner wall surface of the first electrode (31) to detect a temperature of the liquid fluid via the first electrode (31), and a lead (62) configured to support the sensing portion (61). The first electrode (31) is located such that an outer wall surface of the first electrode (31) is exposed in the liquid fuel, and the lead (62) has one end portion connected to the sensing portion (61) and the other end portion connected to a plate portion (53) attached to the housing. Furthermore, an elastic deformation portion (63) is provided as a part of the lead (62), and is configured to be elastically deformed and to cause the sensing portion (61) to be biased in a direction on which the sensing portion (61) contacts the inner wall surface of the first electrode (31).

In the above embodiment, the other portions of the fuel property sensor may be suitably modified.

(Other Embodiments)

The present invention is not limited to the above-described embodiment, and can be modified in various ways without departing from the scope of the invention.

For example, in the above-described embodiment, the present invention is typically applied to a fuel property sensor of an electric capacitance type, which measures an electric capacitance of a liquid fluid to be detected (e.g., a liquid fuel) by using a pair of the first electrode 31 and the second electrode 41 opposite to each other, and detects the fuel property based on the measured electric capacitance. However, the present invention may be applied to a fuel property sensor which measures an impedance of the liquid fuel to be detected, and determines a fuel property of the liquid fuel based on the detected impedance. In an electrode portion for detecting the impedance, the first and second electrodes as the electrode portion are unnecessary to be opposite to each other if the electrode portion is exposed in the liquid fuel directly.

While the invention has been described with reference to preferred embodiments thereof, it is to be understood that the invention is not limited to the above embodiments and constructions. The invention is intended to cover various modification and equivalent arrangements. In addition, while the various combinations and configurations, which are preferred, other combinations and configurations, including more, less or only a single element, are also within the spirit and scope of the invention.

What is claimed is:

1. A fuel property sensor comprising:
    a housing defining a liquid fluid chamber in which a liquid fluid passes;
    a pair of first and second electrodes arranged in the liquid fluid chamber, the first electrode being located such that an outer wall surface of the first electrode is exposed in the liquid fluid passing in the liquid fluid chamber;
    a sensing portion contacting an inner wall surface of the first electrode opposite to the outer wall surface, to detect a temperature of the liquid fluid via the first electrode;
    a support portion adapted as a lead of the sensing portion to support the sensing portion, the support portion having one end portion connected to the sensing portion and the other end portion connected to a plate portion attached to the housing;
    an elastic deformation portion provided as a part of the support portion, wherein the elastic deformation portion is configured to be elastically deformed and to cause the sensing portion to be biased in a direction on which the sensing portion contacts the inner wall surface of the first electrode; and
    a holder fixed to the plate portion, and disposed to be engaged with the inner wall surface of the first electrode, wherein the holder has a receiving portion in which the elastic deformation portion is held to be electrically insulated from the first electrode.

2. A fuel property sensor according to claim 1, wherein a part of the support portion is bent to have a bent portion, and the elastic deformation portion is configured by the bent portion.

3. A fuel property sensor according to claim 1, wherein
    the holder has therein a plurality of communication passages communicating with the receiving portion, at an end side connected to the plate portion, and
    the support portion has a plurality of support parts which are respectively received in the communication passages.

4. A fuel property sensor according to claim 1, wherein the sensing portion is located outside of the holder.

5. A fuel property sensor according to claim 1, wherein the elastic deformation portion is located to be not in contact with the inner wall surface of the first electrode.

6. A fuel property sensor according to claim 1, wherein the first electrode has a cylindrical shape having a bottom.

7. A fuel property sensor according to claim 1, wherein the second electrode is located opposite to the first electrode.

8. A fuel property sensor according to claim 1, wherein the second electrode has an approximately cylindrical shape, and the first electrode is disposed inside of the second electrode.

* * * * *